United States Patent [19]

Nugent

[11] Patent Number: 4,646,753
[45] Date of Patent: Mar. 3, 1987

[54] BLOOD COLLECTOR FOR MICROCOLLECTION CONTAINER

[75] Inventor: Edward L. Nugent, North Caldwell, N.J.

[73] Assignee: Becton, Dickinson and Company, Franklin Lakes, N.J.

[21] Appl. No.: 743,534

[22] Filed: Jun. 11, 1985

[51] Int. Cl.[4] .............................................. A61B 5/14
[52] U.S. Cl. .................................... 128/763; 128/767
[58] Field of Search .................... 128/760, 761–768, 128/770–771

[56] References Cited

U.S. PATENT DOCUMENTS

| 4,024,857 | 5/1977 | Blecher et al. | 128/763 |
|---|---|---|---|
| 4,215,700 | 8/1980 | Crouther et al. | 128/763 |
| 4,250,893 | 2/1981 | White | 128/767 X |
| 4,397,318 | 8/1983 | Burns | 128/763 |
| 4,411,163 | 10/1983 | White | 73/864.02 |

Primary Examiner—Kyle L. Howell
Assistant Examiner—Angela D. Sykes
Attorney, Agent, or Firm—John L. Voellmicke

[57] ABSTRACT

A blood collector, for a microcollection container having an open end, a closed end and a container side wall therebetween, includes a cap for engaging the open end of a container and an elongate body extending through the cap defining a longitudinal axis and having a blood flow passageway therethrough. The body includes a distal front end portion adapted to receive blood from a wound and a proximal rear end portion terminating in a proximal edge for carrying blood to an interior surface of the container side wall. A vent is provided in said cap for air displacement therethrough. The rear end portion includes a generally longitudinally extending discontinuity interrupting the proximal edge for up to substantially about 120° along the periphery of the body in a portion of the rear end portion being substantially adjacent to an interior surface of the container side wall when the cap engages a container. The discontinuity includes side walls extending from the blood flow passageway through the body.

22 Claims, 9 Drawing Figures

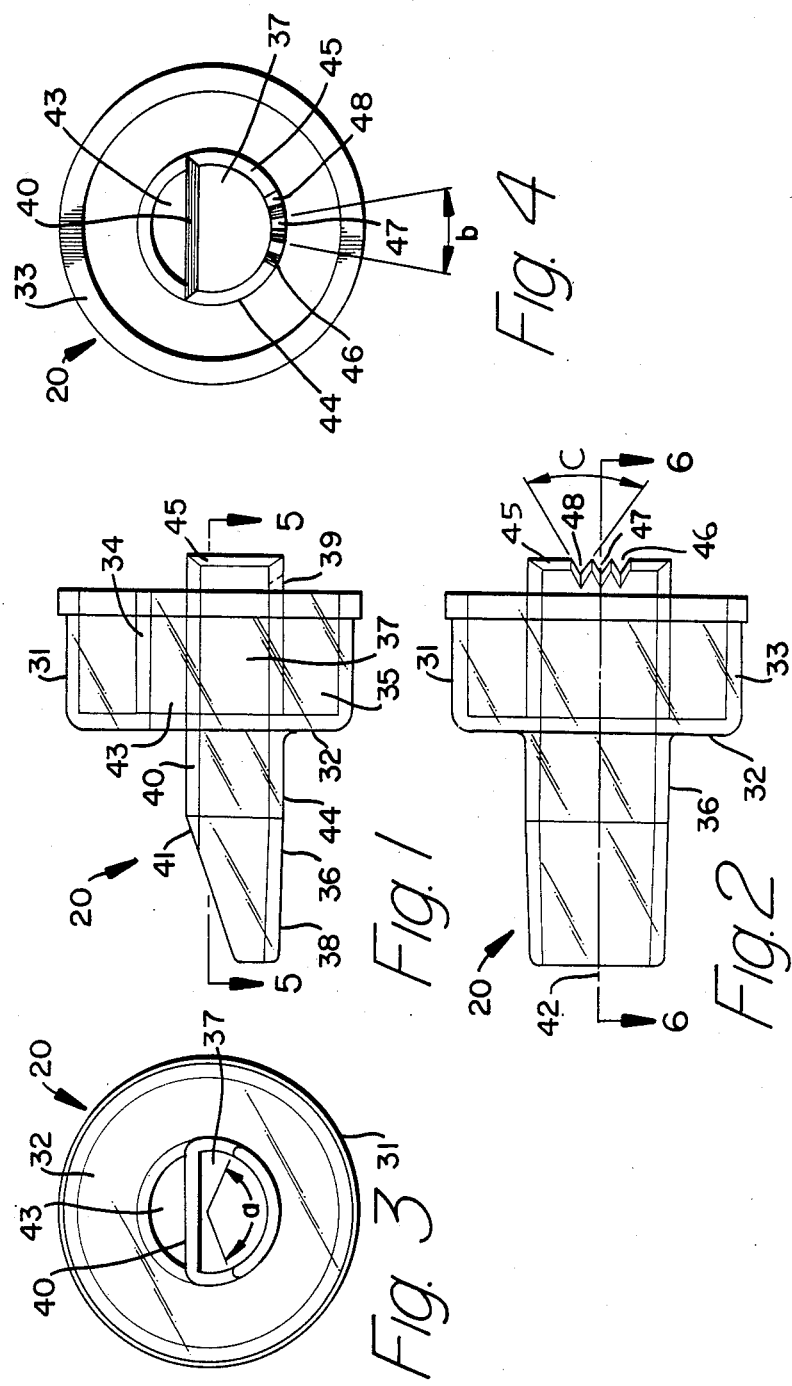

BLOOD COLLECTOR FOR MICROCOLLECTION CONTAINER

BACKGROUND OF THE INVENTION

The present invention relates to a blood collector for a microcollection container and more particularly concerns a blood collector having an improved configuration of the blood flow passageway.

DESCRIPTION OF THE PRIOR ART

Advancements in analytical instrumentation have made it possible to carry out a variety of hematological diagnostic procedures on very small quantities of blood. Accordingly, a patient's finger or earlobe, for example, may be punctured or cut and a very small quantity of capillary blood rapidly collected into a microcollection container for subsequent analysis. Such arrangements minimize the need for withdrawing a larger quantity of venous blood from the patient.

U.S. Pat. No. 4,024,857 to Blecher et al. teaches a device for collecting blood from several capillaries including a cup, a removable vented top attached to the open end of the cup and a capillary tube passing through the top. The distal end of the capillary tube is outside of the cup and the proximal end of the capillary tube is in contact or near the inside wall of the cup. Blecher et al. teach that the placement of the capillary tube adjacent to or in contact with the inside wall of the cup provides faster more uniform blood flow from the source to the interior of the cup than if the capillary tube was positioned centrally in the cup away from the interior walls.

U.S. Pat. No. 4,397,318 to Burns teaches an improved micro blood collection device. Burns teaches that a microcollection device using a capillary tube has some shortcomings in that, in use, the tip of the capillary must be positioned precisely adjacent to the puncture wound and the entire device should be angularly oriented so that the blood flow through the capillary is along the lowest surface of the tubular side wall of the microcollection cup in order for blood from the capillary tube to engage the surface of the container. If this precise positioning is not carried out, the smooth transition of blood from the wound to the microcollection cup may be compromised and, further, the blood flow may be slowed to a point where clotting may affect the ability of the device to obtain a full sample. Burns teaches a blood collector having a large scoop shaped conduit for blood flow in place of a capillary tube. Specifically, Burns teaches a cap which incorporates a partially open tubular and tapered scoop arrangement for engaging a puncture wound and rapidly receiving blood from the wound. The scoop is such that a substantial end surface is provided for engaging a puncture wound for receiving blood, and rapidly transferring it to a microcollection container where a further large abutting angular surface engages the surface of the microcollection container. With this invention, the time of transfer is reduced because of the less precise positioning and orientation requirement of the scoop and the apparent elimination of the need to initiate a capillary action.

In collecting capillary blood using microcollection devices there is a tendency for the blood specimen to accumulate in the passageway of the collector and not readily flow over the transition between the collector and the inside wall of the reservoir. However, providing additional blood and/or holding the container at a steeper angle will help initiate this flow. It is very desirable to obtain the capillary blood sample as quickly as possible in order to minimize the potential for clotting and also in situations where the subject, such as an infant, must be temporarily restrained during the sampling procedure. Although the tendency for the blood sample to "hang-up" at the transition between the collector and the reservoir inside wall is a momentary phenomenon, it is undesirable because it can delay the collection procedure.

There is a need for an improved blood collector which provides for the more rapid transition of the blood sample from the collector into the reservoir and which minimizes the amount of blood necessary for transition of the blood sample from the collector into the reservoir.

SUMMARY OF THE INVENTION

The blood collector of the present invention, for use with a microcollection container having an open end, a closed end and a container side wall therebetween, comprises a cap for engaging the open end of a container and an elongate body extending through the cap defining a longitudinal axis and having a blood flow passageway therethrough. The body also includes a scoop-shaped distal front end portion adapted to receive blood from a wound and a proximal rear end portion terminating in a proximal edge for carrying blood to an interior surface of the container side wall. Vent means is provided in the cap for air displacement therethrough. The rear end portion of the body includes a generally longitudinally extending discontinuity interrupting the edge for up to substantially about 90° along the periphery of the body in a portion of the rear end portion being substantially adjacent to an interior surface of the container side wall when the cap engages a container. The discontinuity has side walls extending from the blood flow passageway through the body.

In accordance with another embodiment of the present invention, a blood collector, for use with a tube-shaped microcollection container having an open end, a closed end and a container side wall therebetween, comprises a cap for engaging the open end of a microcollection container and a semicircular body extending through the cap defining a longitudinal axis and having a blood flow passageway therethrough. The body is positioned with respect to the cap so that a portion of the body is adjacent to an interior surface of the container side wall when the cap engages a container. The body includes a distal front end portion adapted to receive blood from a wound and a proximal rear end portion terminating in a proximal edge for carrying blood to an interior surface of the container side wall. Vent means is provided in the cap for air displacement therethrough. A vane portion of the body separates the vent means from the blood flow passageway. This vane portion extends through the cap to a point spaced from the distal most portion of the front portion to form a semi-tubular scoop means. The rear end portion of the body includes a plurality of generally longitudinally extending discontinuities each of which interrupts the edge for up to substantially about 30° along the circumference of the body so that at least one of the discontinuities is substantially adjacent to an interior surface of the container side wall when the cap engages a microcollection container. The discontinuities have side walls extending from the blood flow passageway through the body.

In accordance with the principles of the present invention, a number of advantages and objectives are attained. The present invention provides a simple straight-forward, reliable, easily fabricated blood collector for use with a microcollection container or reservoir for collecting capillary blood samples. As will be hereinafter shown, the present invention provides structure to facilitate the more rapid transition of the blood sample from the collector into the microcollection container or reservoir and minimizes the amount of blood necessary for transition of the blood sample from the collector into the reservoir.

BRIEF DESCRIPTION OF THE DRAWINGS

FIG. 1 is a side elevation view of the preferred blood collecter of the present invention;

FIG. 2 is a bottom plan view of the preferred blood collector;

FIG. 3 is a distal end view of the preferred blood collector;

FIG. 4 is a proximal end view of the preferred blood collector;

DETAILED DESCRIPTION

Figure 5:
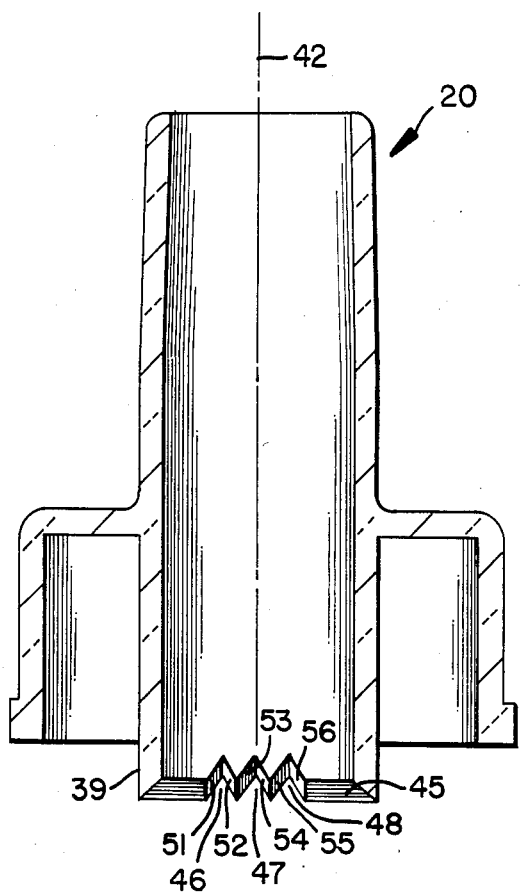
FIG. 5 is a cross-sectional view of the blood collector of FIG. 1 taken along line 5—5.
Figure 6:
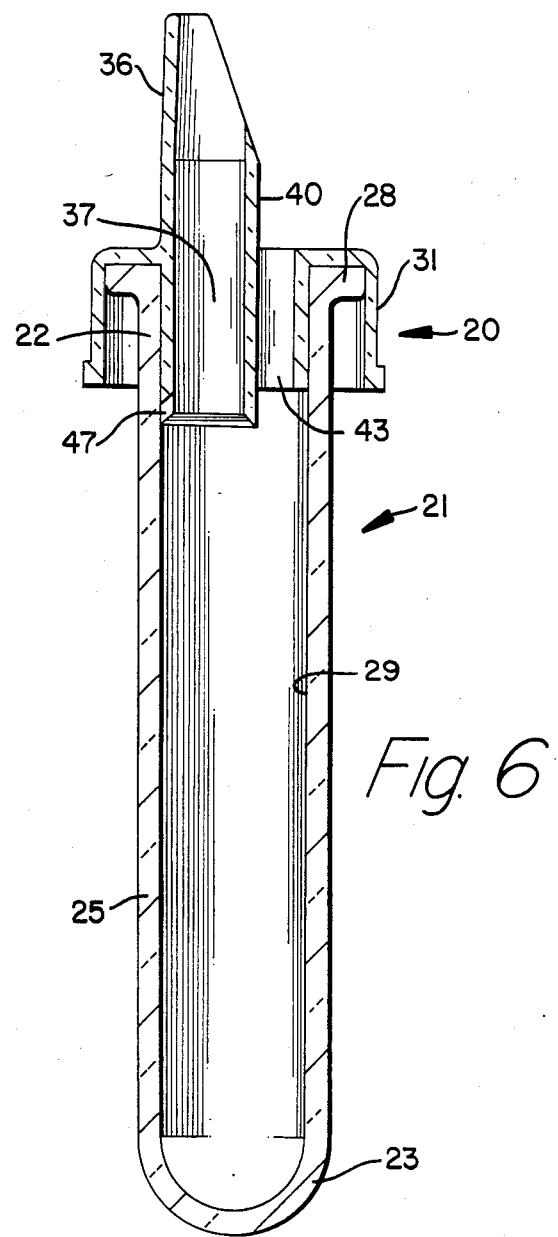
FIG. 6 is a side elevation cross-sectional view of the preferred blood collector of FIG. 2 taken along line 6—6 along with a microcollection container engaging the preferred blood collector.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting to FIGS. 1-7, a blood collector 20 is for use with an elongate microcollection container or reservoir 21 having an open end 22, a closed end 23 and a cylindrically shaped side wall 25. Container 21 also includes enlarged neck portion 28 and an interior surface 29 of the side wall. It is within the purview of the present invention to include microcollection containers having side walls of various cross-sectional shapes, and that the microcollection container described herein, having a circularly shaped cross sesction is exemplary of these many possibilities.

Blood collector closure 20 includes a cap or cap portion 31 for removably engaging open end 22 of the microcollection container. The cap portion includes top wall 32, annular skirt 33 and interior annular skirt 34. An annular space 35 defined by the spaced skirts 33 and 34 defines a space for receiving the open end of the microcollection container in an interference or press-fit arrangement. It will be apparent to one skilled in the art that numerous constructions can be used to provide a cap capable of removably engaging a microcollection container, such as structure having threads, structure providing for a snap-fit, structure engaging the inside of the microcollection container in a press-fit arrangement etc. and that the arrangement described herein is exemplary of these many possibilities.

A longitudinally extending, semicircular body 36, defining a longitudinal axis 42, is incorporated into the cap and extends therethrough from a scoop-shaped distal front end portion 38 to a proximal rear end portion 39 having a blood flow passageway 37 therethrough. For purposes of the description of the present invention, the term "distal end" is meant to refer to the end furthest from the person holding the microcollection container and the end closest to the source of blood, whereas the term "proximal end" is meant to refer to the end closest to the holder of the container or reservoir.

As will be explained in more detail hereinafter, body 36 is positioned with respect to cap portion 31 so that a portion of the body is adjacent to or touching interior surface 29 of side wall 25 of the container when the cap engages the container.

A flat vane portion 40 of the body extends through the cap preferably but not necessarily to proximal rear end portion 39, on one side, and to a point preferably spaced from front end portion 38 on the other side, to form a semi-tubular scoop. As best illustrated in FIG. 3, the body of the scoop at front end portion 38 extends for approximately 120°, shown as angle a in FIG. 3. Moving proximally from this point, the scoop body becomes larger until it merges into the vane portion at 41.

A longitudinally oriented venting conduit or vent area 43 is defined between interior annular skirt 34 and vane portion 40 of the body. The vent area provides a conduit for air to exit from the microcollection container when blood is introduced into the container through blood flow passageway 37.

Vane portion 40 and a circular portion 44 of body 36 define the blood transfer passageway 37 for rapidly transferring a quantity of blood from the surface of the patient's skin adjacent to the severed capillaries to the interior of the microcollection tube. Rear end portion 39 of body 36 preferably has a semi-circular proximal edge 45, which, in this embodiment, preferably extends for approximately 240° at which point circular portion 44 of the body joins vane portion 40 of the body. In the preferred embodiment, proximal edge 45 is tapered in a direction toward the outside bottom edge of the body so that the wall of the body becomes thinner as it approaches the proximal end. In prior art devices, such as the U.S. Pat. No. 4,397,318 to Burns alluded to hereinabove, the proximal edge is smooth and continuous throughout its length. However, in the instant preferred embodiment there are a plurality of generally longitudinally extending discontinuities, illustrated as 46, 47 and 48, wherein each discontinuity extends for approximately 20° along the circumference of the body as best illustrated in FIG. 4 as angle b. It is desirable that each discontinuity should occupy no more than about 90° along the circumference of the body in a portion of the rear edge portion, with discontinuities up to about 15° to 30° being preferred.

Discontinuities 46, 47 and 48 have side walls 51 through 56 respectively. These side walls are also inclined in the same direction as proximal edge 45. In this preferred embodiment the series of substantially similarly shaped discontinuities forms a zig zag or saw tooth like shape having preferably straight side walls wherein the side walls within each discontinuity are desirably inclined at approximately 30 to 90 degrees with respect to each other, as best illustrated in FIG. 2 as angle c, which is preferably 60° wherein each tooth is a discontinuity touching at least one adjacent discontinuity. However, it is within the purview of the present invention to include discontinuities having curved or curvilinear side walls. It is within the purview of the present invention to include blood collectors wherein the discontinuities are not substantially similarly shaped and collectors wherein the discontinuities are in a spaced relationship, separated by portions of the proximal edge. As will be explained in more detail hereinafter, it is also within the purview of the present invention to include discontinuities which project generally longitudinally outwardly from edge 45 as well as those that project generally longitudinally inwardly from edge 45 and combinations thereof.

As will be appreciated by those skilled in the art, it is most important for small quantities of blood, from the severed capillaries, to be transferred rapidly into the collection container. The steady flow of blood from the patient to the microcollection container is facilitated if the blood can easily travel over the transition between the proximal end of the blood flow passageway onto the interior surface of the side wall of the microcollection container. Experimental data indicates, in a comparison between collectors having the preferred saw tooth shaped discontinuities and those having a straight uninterrupted proximal edge running substantially perpendicularly to the longitudinal axis of the collector, that when applying 25 microliter drops of blood to the test collectors which are inclined downwardly at a 45 degree angle from the horizontal it takes, on average, about six drops of blood in the blood flow conduit to initiate flow from the collector, having an uninterrupted proximal edge, into the microcollection container. By contrast, only about two drops are required, on average, to initiate flow using a collector substantially similar to the preferred embodiment described herein.

Figure 7:
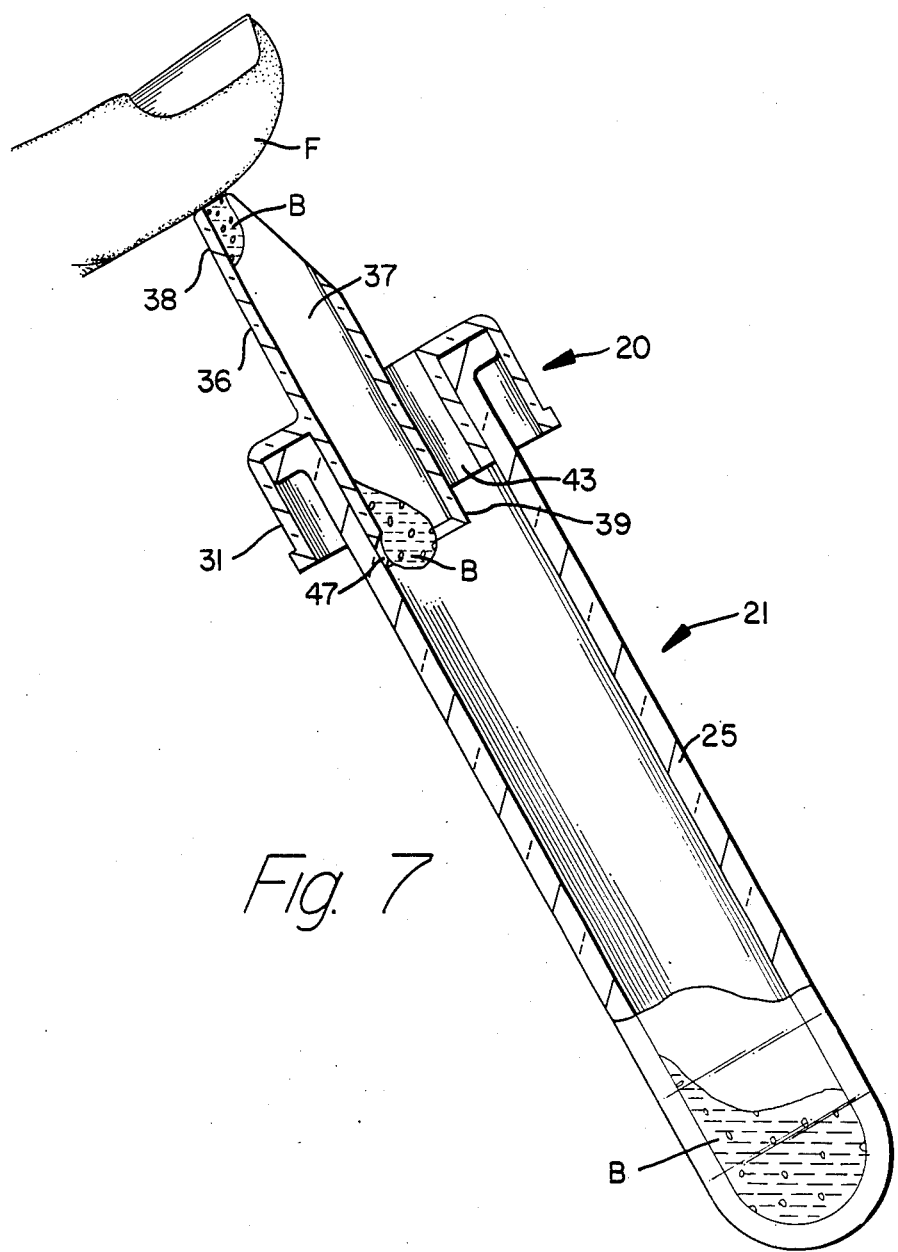
FIG. 7 is a partially cross-sectioned side elevation view of the assembly of the preferred blood collector and a microcollection tube, schematically showing the collection of a blood sample from a patient.

In use, a known lancet is used to sever the patient's skin, for example at finger F, in FIG. 7, to severe blood capillaries so that the blood will escape to the surface of the skin. At this time, the blood collector of the present invention, attached to microcollection container 21, is positioned near the cut produced by the lancet and inclined downwardly so that the blood will enter scoop-shaped distal front end portion 38, travel through blood flow passageway 37 to rear end portion 39 wherein the blood B passes over the semi-circular proximal edge and one or more of the discontinuities, and into the microcollection container. When a full sample is taken, the collector may be removed from the microcollection container by using a twisting and/or pulling motion to overcome the interference fit between the collector and the container, and then the sample may be covered with a separate cover, not shown, and transported to the appropriate test area. The enlarged neck portion 28 of the collector acts as a flange allowing the collector to be centrifuged to separate the serum or plasma for analysis.

Figure 8:
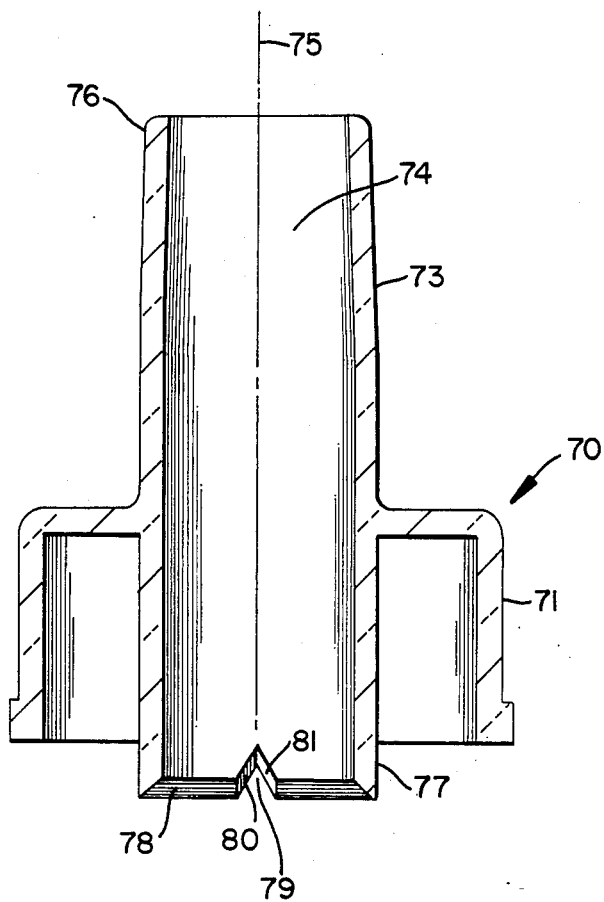
FIG. 8 is a top plan view of an alternative embodiment of the blood collector of the present invention.

Referring now to FIG. 8, an alternative blood collector 70, for use with a microcollection container (not shown) having an open end, a closed end and a container side wall therebetween, is similar to the preferred blood collector 20 described hereinabove. Blood collector 70 includes a cap 71 for removably engaging the open end of a microcollection container and an elongate body 73 extending through the cap and having a blood flow passageway 74 defining a longitudinal axis 75. The body includes a scoop-shaped distal front end portion 76 for receiving blood and a proximal rear end portion 77 terminating in a proximal edge 78, for carrying blood to an interior surface of the side wall of a microcollection container. The rear end portion of this embodiment includes a longitudinally extending discontinuity 79 interrupting edge 78 for about 30° along the periphery of the body in a portion of the rear end portion which is substantially adjacent to the container side wall when the cap engages the microcollection container. Discontinuity 79 includes side walls 80 and 81. In this embodiment the discontinuity extends inwardly from proximal edge 78 and includes substantially straight side walls to form a V-shaped discontinuity wherein the widest portion of the V-shape is closest to the edge. Side walls 80 and 81 inclined preferably at about 60° with respect to each other. It is also within the purview of the present invention to include other inwardly extending discontinuities having curved or curvilinear side walls wherein the discontinuity interrupts the edge for up to but not exceeding approximately about 120°.

Figure 9:
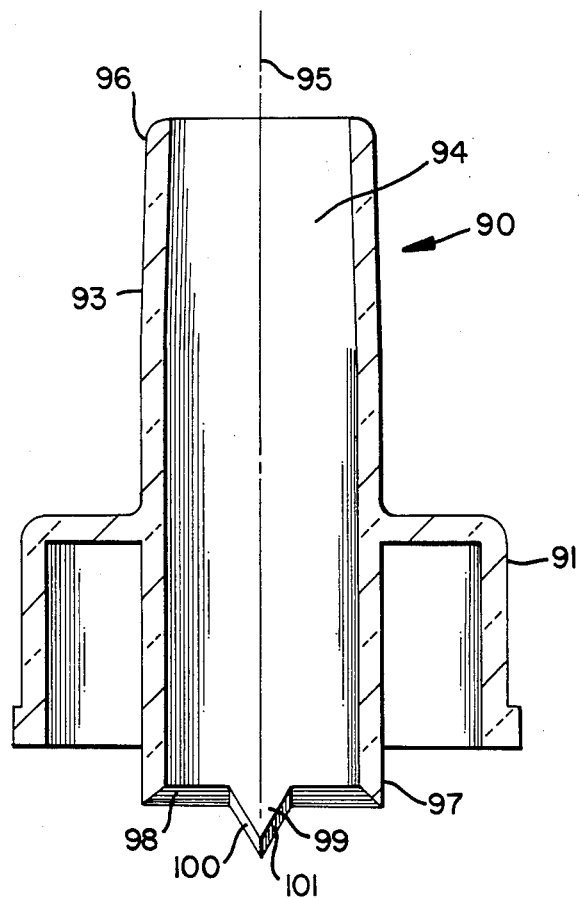
FIG. 9 is a top plan view of another alternative embodiment of the blood collector of the present invention.

Referring now to FIG. 9, another alternative embodiment of the instant invention is blood collector 90 includes cap portion 91 for engaging the open end of a microcollection container (not shown) and an elongate body 93 extending through the cap and having a blood flow passageway 94 defining longitudinal axis 95. The semi-circular body includes a distal front end portion 96 adapted to receive blood from a wound and a proximal rear end portion 97 terminating in proximal edge 98. Rear end portion 97 includes a generally longitudinally extending discontinuity 99 interrupting edge 98 for approximately 30 degrees along the periphery of the body in a portion of the rear end portion being substantially adjacent to an interior surface the container side wall when the cap engages a container. Discontinuity 99 extends outwardly from edge 98 increasing the general longitudinal length of rear end portion 97 in the area of the discontinuity. The discontinuity of this alternative embodiment is V-shaped wherein the widest portion of the V-shape is closest to edge 98. Discontinuity 99 includes substantially straight side walls extending from the conduit through the body. It is also within the purview of the instant invention to include other outwardly extending discontinuities having curved and-/or curvilinear shapes wherein each discontinuity interrupts the edge for no more than about 120° along the circumference or the periphery of the body in a portion of the rear end portion being substantially adjacent to an interior surface of the microcollection container side wall when the cap engages a container.

While the blood collector closure of the present invention may have a body separately configured to be inserted into a cap portion wherein each of the components can be constructed separately and of different materials, it is preferred that the blood collector of the present invention be of an integral structure. A wide variety of materials may be used to form the blood collector of the present invention with plastic being preferred. It is also preferred that the blood collector of the present invention be constructed of transparent and/or translucent materials so that the user can observe the blood flow through the collector. A wide variety of plastic materials are desirable with clear or translucent polyethylene being preferred. Also, a wide variety of rigid materials may be suitable for forming a microcollection container or reservoir with plastic materials such as polypropylene being preferred.

Thus, it can be seen that the present invention provides a simple straight-forward, reliable, easily fabricated blood collector for use with a microcollection container. The instant invention provides improvements over prior art blood collectors in that it provides for more rapid transition of the blood sample from the collector into the microcollection container or reservoir and minimizes the amount of blood necessary for transition of the blood sample from the collector into the reservoir.

What is claimed is:

1. A blood collector, for an elongate microcollection container having an open end, a closed end and a container side wall therebetween, comprising:
    a cap for removably engaging the open end of a microcollection container;
    an elongate body extending through said cap defining a longitudinal axis, said body having a blood flow passageway therethrough, said body being positioned with respect to said cap so that a portion of said body is adjacent to an interior surface of the container side wall when said cap engages the container;
    a distal front end portion of said body adapted to receive capillary blood from a wound;
    a proximal rear end portion of said body terminating in a proximal edge for carrying blood to an interior surface of the container side wall;
    vent means in said cap for air displacement therethrough;
    a vane portion of said body separating said vent means from said passageway;
    said rear end portion including a generally longitudinally extending discontinuity interrupting said edge for up to substantially about 120° along the periphery of said body in a portion of said rear end portion being substantially adjacent to an interior surface of the container side wall when said cap engages a microcollection container, said discontinuity having side walls extending from said blood flow passageway through said body.

2. The blood collector of claim 1 wherein said discontinuity extends inwardly from said edge into said rear end portion.

3. The blood collector of claim 2 wherein said side walls of said discontinuity are substantially straight.

4. The blood collector of claim 2 wherein said discontinuity is V-shaped wherein the widest portion of the V-shape is closest to said edge.

5. The blood collector of claim 1 wherein said discontinuity extends outwardly from said edge increasing the general longitudinal length of said rear end portion in the area of said discontinuity.

6. The blood collector of claim 5 wherein said side walls of said discontinuity are substantially straight.

7. The blood collector of claim 5 wherein said discontinuity is V-shaped wherein the widest portion of the V-shape is closest to said edge.

8. The blood collector of claim 1 having a plurality of discontinuities.

9. The blood collector of claim 8 wherein each of said discontinuities extends for up to substantially about 30° along the circumference of said body.

10. The blood collector of claim 9 wherein said discontinuities are substantially similarly shaped.

11. The blood collector of claim 10 wherein said side walls of said discontinuities are substantially straight.

12. The blood collector of claim 8 wherein said discontinuities are in a spaced relationship separated by portions of said edge.

13. The blood collector of claim 1 in combination with a microcollection container having an open end, a closed end and a container side wall therebetween, said cap releasably sealing said open end of said container so that said proximal rear end portion of said body is within said container and said discontinuity being substantially adjacent to an interior surface of said container side wall and said distal front end portion of said body extending outwardly from said container.

14. The blood container closure of claim 1 wherein said side walls of said discontinuity are oriented in a direction substantially perpendicular to said longitudinal axis.

15. The blood collector of claim 1 wherein said cap and said body are of integral construction.

16. The blood collector of claim 15 wherein said blood collector is made of thermoplastic material.

17. A blood collector, for a microcollection container having an open end, a closed end and a container side wall therebetween, comprising:
    a cap for engaging the open end of a container;
    an elongate body extending through said cap defining a longitudinal axis, said body having a blood flow passageway therethrough,
    a distal front end portion of said body adapted to receive blood from a wound;
    a proximal rear end portion of said body terminating in a proximal edge for carrying blood to an interior surface of the container side wall;
    vent means in said cap for air displacement therethrough; and
    said rear end portion including a generally longitudinally extending discontinuity interrupting said proximal edge for up to substantially about 120° along the periphery of said body in a portion of said rear end portion being substantially adjacent to an interior surface of the container side wall when said cap engages a container, said discontinuity having side walls extending from said blood flow passageway through said body.

18. A blood collector, for a tube-shaped microcollection container having an open end and a closed end and a container side wall therebetween, comprising:
    a cap for engaging the open end of a microcollection container;
    a semi-circular body extending through said cap defining a longitudinal axis, said body having a blood flow passageway therethrough, said body being positioned with respect to said cap so that a portion of said body is adjacent to an interior surface of the container side wall when said cap engages the container;
    a distal front end portion of said body adapted to receive blood from a wound;
    a proximal rear end portion of said body terminating in a proximal edge for carrying blood to an interior surface of the container side wall;
    vent means in said cap for air displacement therethrough;

a vane portion of said body separating said vent means from said passageway, said vane portion extending through said cap; and said rear end portion including a plurality of generally longitudinally extending discontinuities each of which interrupt said edge for up to substantially about 30° along the circumference of said body so that at least one of said discontinuities is substantially adjacent to an interior surface of the container side wall when said cap engages a microcollection container, said discontinuities having side walls extending from said blood flow passageway through said body.

19. The blood collector of claim 18 wherein said discontinuities are substantially similarly shaped.

20. The blood collector of claim 19 wherein said discontinuities form a saw tooth shaped surface, each tooth being a discontinuity touching at least one adjacent discontinuity.

21. The blood collector of claim 18 wherein said side walls of said discontinuities are substantially straight.

22. The blood collector of claim 18 wherein said discontinuities are in a spaced relationship separated by portions of said edge.

* * * * *